United States Patent [19]
Fleischman et al.

[11] Patent Number: 6,030,382
[45] Date of Patent: *Feb. 29, 2000

[54] FLEXIBLE TISSUE ABLATIN ELEMENTS FOR MAKING LONG LESIONS

[75] Inventors: Sidney D. Fleischman, Menlo Park; Russell B. Thompson, Los Altos; Dorin Panescu, Sunnyvale; David K. Swanson, Mountain View, all of Calif.

[73] Assignee: EP Technologies, Inc., San Jose, Calif.

[ * ] Notice: This patent is subject to a terminal disclaimer.

[21] Appl. No.: 09/055,175

[22] Filed: Apr. 3, 1998

Related U.S. Application Data

[63] Continuation-in-part of application No. 08/558,131, Nov. 13, 1995, Pat. No. 5,797,905, which is a continuation-in-part of application No. 08/287,192, Aug. 8, 1994, abandoned, and a continuation-in-part of application No. 08/439,824, May 12, 1995, abandoned.

[51] Int. Cl.[7] .................................................. A61B 17/36
[52] U.S. Cl. ............................ 606/41; 600/374; 607/102; 606/42
[58] Field of Search ........................... 606/41, 42, 45–50; 607/101, 102, 122; 600/374

[56] References Cited

U.S. PATENT DOCUMENTS

| | | |
|---|---|---|
| 4,633,889 | 1/1987 | Tallalla et al. . |
| 4,960,133 | 10/1990 | Hewson . |
| 5,016,808 | 5/1991 | Heil, Jr. et al. . |
| 5,047,026 | 9/1991 | Rydell . |
| 5,254,088 | 10/1993 | Lundquist et al. . |
| 5,330,518 | 7/1994 | Neilson et al. ........................ 607/101 |
| 5,334,193 | 8/1994 | Nardella . |
| 5,383,876 | 1/1995 | Nardella . |
| 5,545,193 | 8/1996 | Fleischman et al. . |
| 5,555,618 | 9/1996 | Winkler . |
| 5,582,609 | 12/1996 | Swanson et al. ........................ 606/39 |
| 5,609,621 | 3/1997 | Bonner ................................... 607/122 |
| 5,628,313 | 5/1997 | Webster, Jr. ............................ 600/374 |
| 5,676,662 | 10/1997 | Fleischhacker et al. . |
| 5,810,803 | 9/1998 | Moss et al. ............................... 606/33 |
| 5,855,578 | 1/1999 | Guglielmi et al. ........................ 606/32 |
| 5,876,398 | 3/1999 | Mulier et al. ............................. 606/41 |

*Primary Examiner*—Michael Peffley
*Attorney, Agent, or Firm*—Henricks, Slavin & Holmes LLP

[57] ABSTRACT

Devices and methods for ablating body tissue. The devices include a support body and at least one elongated electrode. Adjacent windings are spaced apart to impart enhanced flexibility to the elongated electrode.

54 Claims, 11 Drawing Sheets

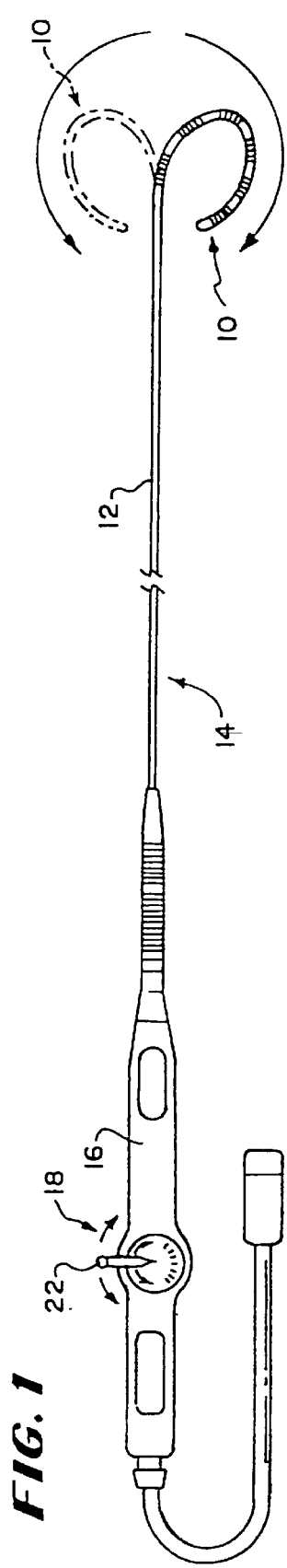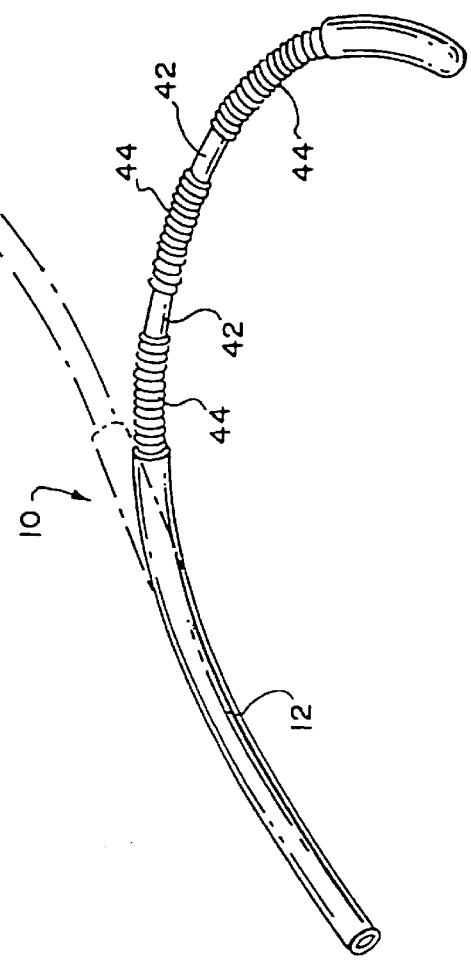

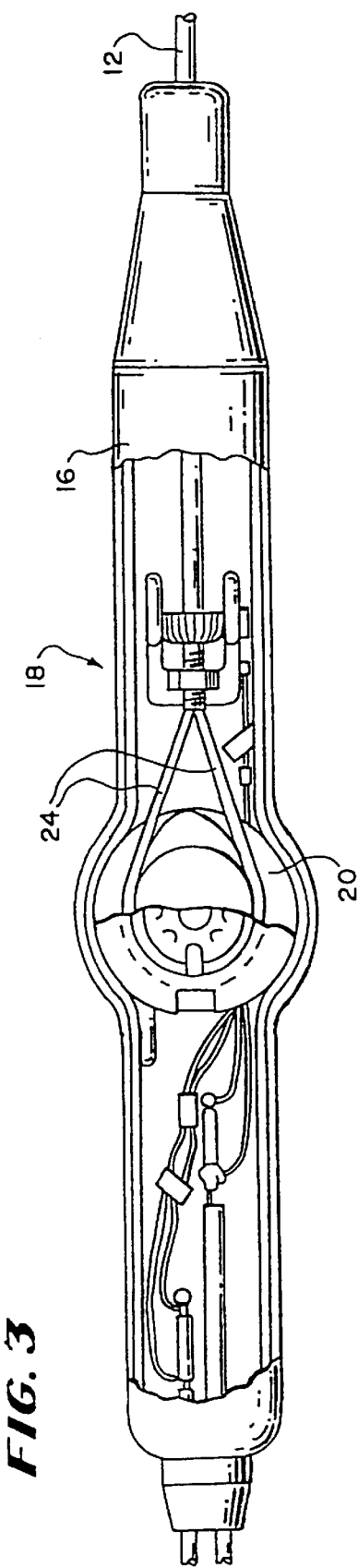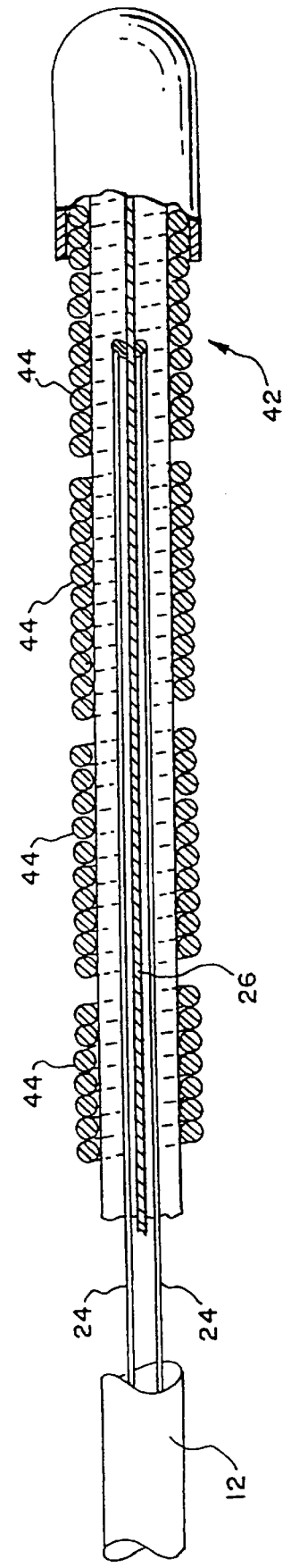
FIG. 3
FIG. 4

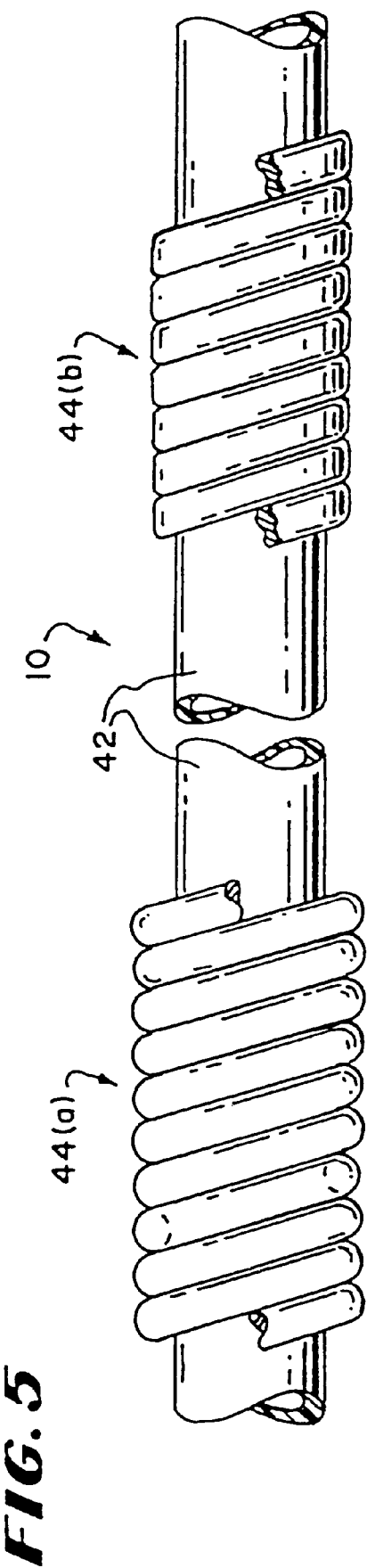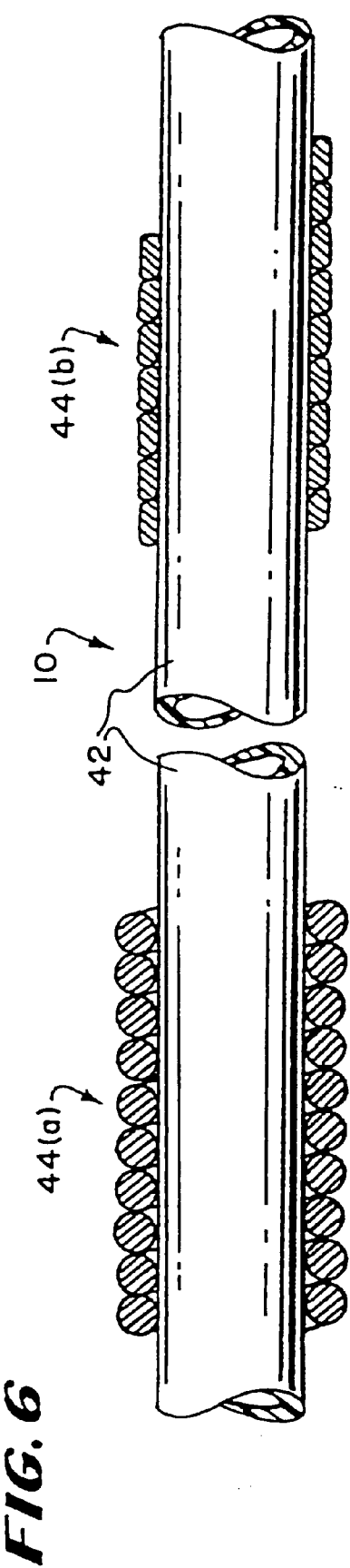

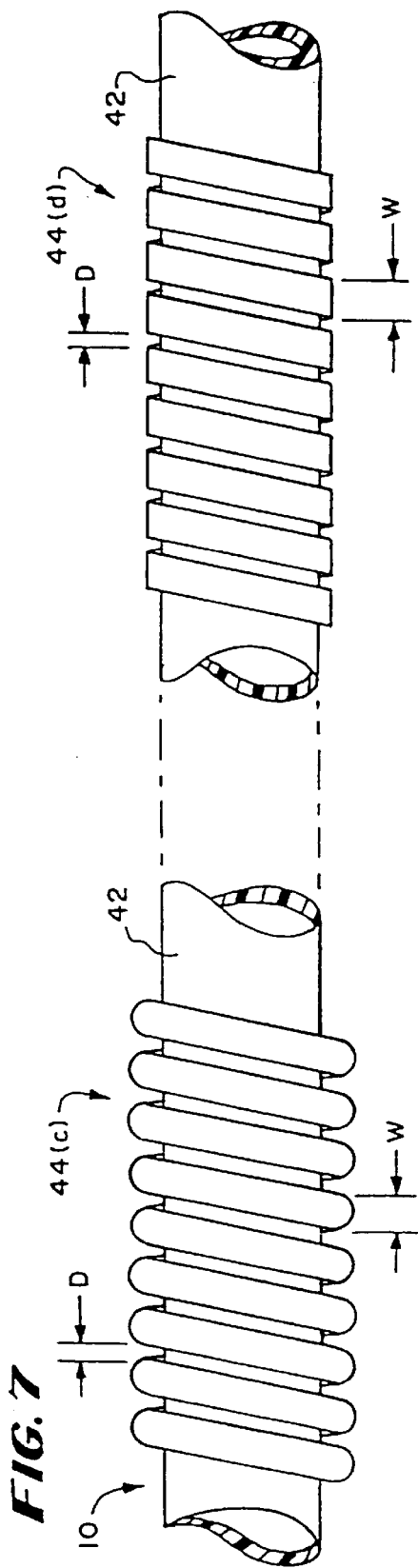
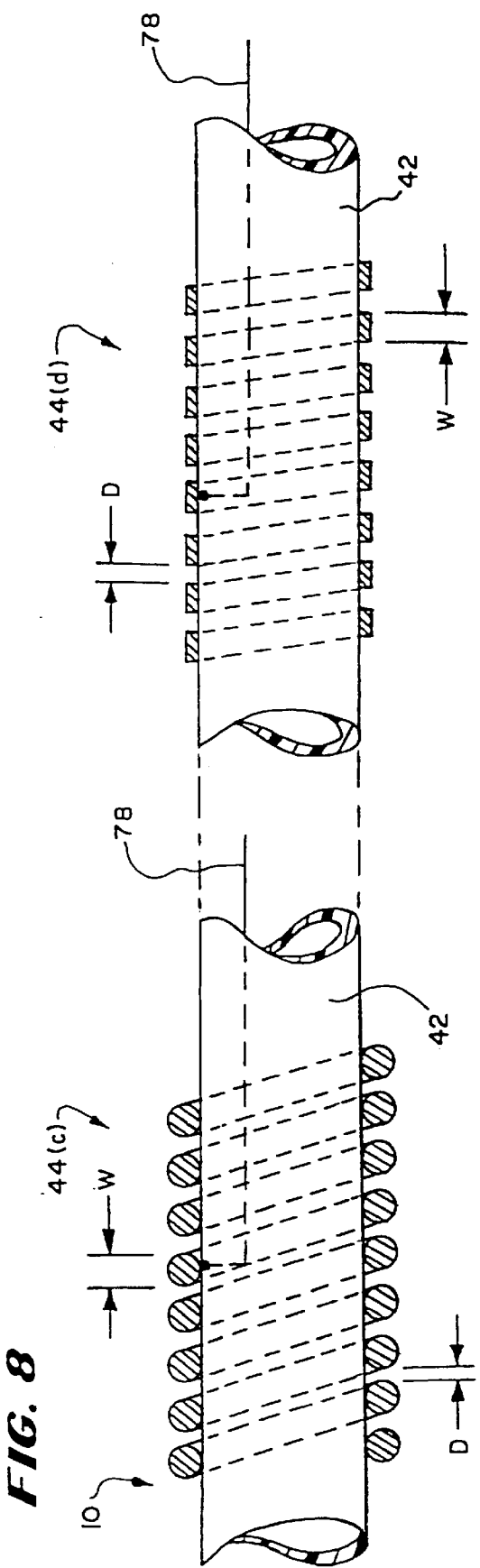

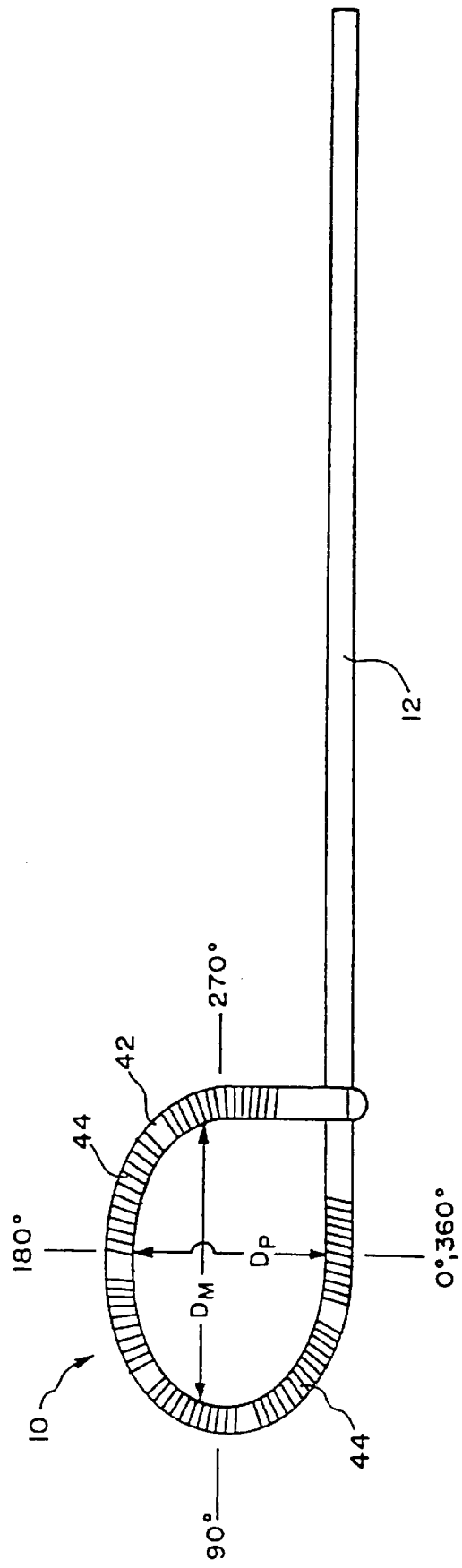

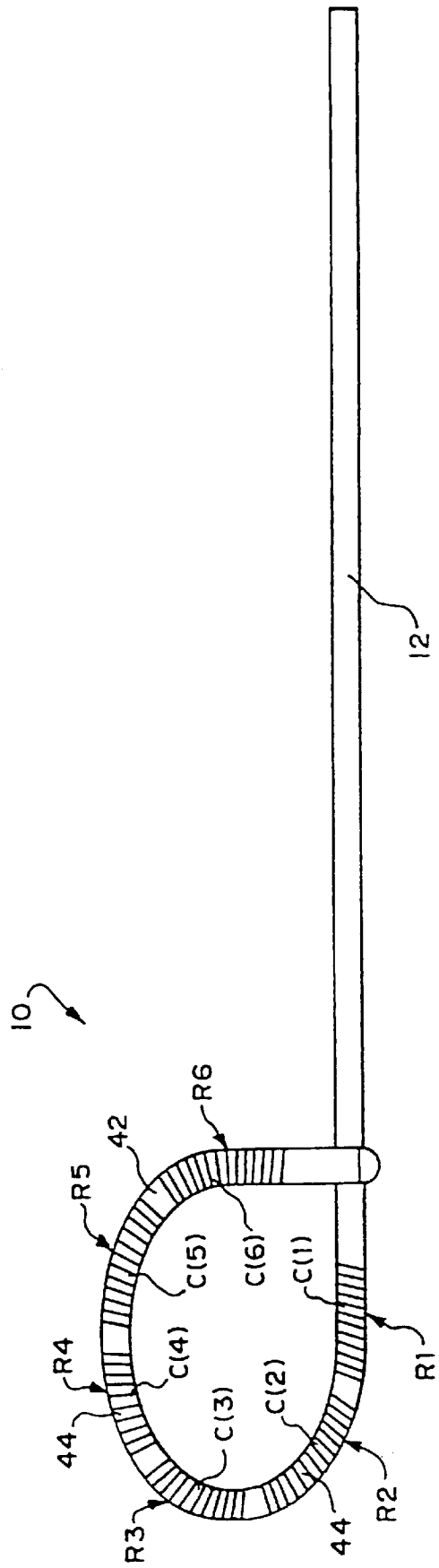

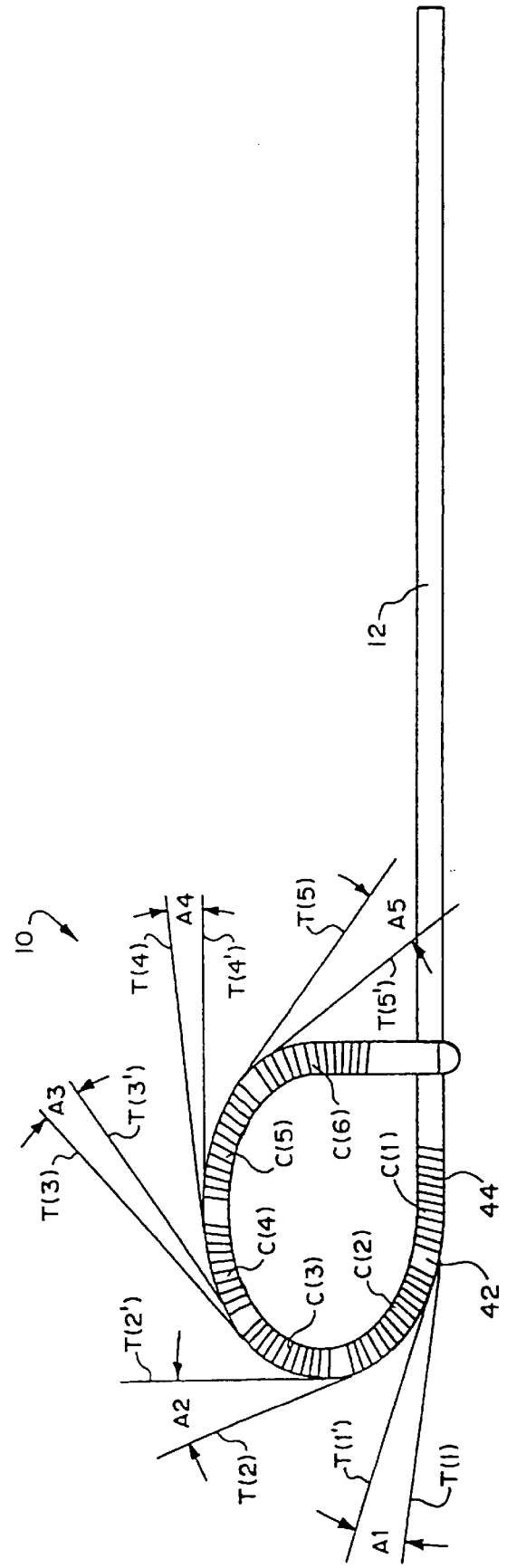

FLEXIBLE TISSUE ABLATIN ELEMENTS FOR MAKING LONG LESIONS

CROSS-REFERENCE TO RELATED APPLICATIONS

This application is a continuation-in-part of U.S. application Ser. No. 08/558,131, filed Nov. 13, 1995, now U.S. Pat. No. 5,797,905, which is itself a continuation-in-part of both U.S. application Ser. No. 08/287,192, filed Aug. 8, 1994, (abandoned) and U.S. application Ser. No. 08/439,824, filed May 12, 1995 (abandoned).

BACKGROUND OF THE INVENTION

1. Field of the Inventions

The inventions relate to systems and methods for ablating tissue such as, for example, systems and methods for ablating myocardial tissue for the treatment of cardiac conditions.

2. Description of the Related Art

Physicians make use of catheters and other devices today in medical procedures to gain access into interior regions of the body to ablate targeted tissue areas. It is important for the physician to be able to precisely locate the device, and control its emission of energy within the body during tissue ablation procedures.

For example, in electrophysiological therapy, ablation is used to treat cardiac rhythm disturbances. During some of these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion.

In electrophysiological therapy, there is a growing need for ablating elements capable of providing lesions in heart tissue and other tissue having different geometries.

For example, it is believed the treatment of atrial fibrillation requires the formation of long lesions of different curvilinear shapes in heart tissue. Such long lesion patterns require the deployment within the heart of flexible ablating elements having multiple ablating regions. The formation of these lesions by ablation can provide the same therapeutic benefits the complex suture patterns that the surgical maze procedure presently provides, but without invasive, open heart surgery.

As another example, it is believed that treatment of atrial flutter and ventricular tachycardia requires the formation of relatively large and deep lesion patterns in heart tissue. Merely providing "bigger" electrodes does not meet this need. Catheters carrying large electrodes are difficult to introduce into the heart and difficult to deploy in intimate contact with heart tissue. However, by distributing the larger ablating mass required for these electrodes among separate, multiple electrodes spaced apart along a flexible body, these difficulties can be overcome.

With larger and/or longer multiple electrode elements comes the demand for more precise control of the ablating process. The delivery of ablating energy must be governed to avoid incidences of unwanted tissue damage and coagulum formation. The delivery of ablating energy must also be carefully controlled to assure the formation of uniform and continuous lesions, without hot spots and/or gaps forming in the ablated tissue.

SUMMARY OF THE INVENTION

The invention provides devices and methods for ablating body tissue. The devices include a support body and at least one elongated electrode. A connection may couple the electrode to a source of ablation energy for transmission by the elongated electrode to ablate tissue. According to the invention, the adjacent windings are spaced apart to impart enhanced flexibility to the elongated electrode.

In a preferred embodiment, the adjacent windings are spaced apart by at least ⅕ of the width of the windings. For example, when wire is used to form the windings, adjacent windings are spaced apart by at least ⅕ of the width of the wire. In a preferred implementation, the windings are spaced apart by about ½ of the width of the windings.

In a preferred embodiment, the elongated electrode has at least one edge adjoining the support body. In this embodiment, the adjacent windings are spaced farther apart away from the edge than at the edge. In one implementation, spacing between adjacent windings varies away from the edge. In another implementation, spacing between adjacent windings is generally uniform away from the edge.

In a preferred embodiment, a temperature sensing element is carried by the electrode near the at least one edge, where the adjacent windings are closer together to support it.

In a preferred embodiment, the connection couples the wire to a source of radio frequency ablation energy for transmission by the elongated electrode to ablate tissue.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 1 is a view of a catheter-type probe that carries a flexible ablating element comprising an array of spaced apart coil electrodes.

FIG. 2 is an enlarged view of the array of spaced apart coil electrodes carried by the probe shown in FIG. 1.

FIG. 3 is an enlarged view of the handle of the probe shown in FIG. 1, with portions broken away and in section, showing the steering mechanism for flexing the ablating element.

FIG. 4 is an enlarged side section view of the ablating element further showing the steering mechanism for flexing the ablating element.

FIGS. 5 and 6 are, respectively, side and side section views of tightly wrapped coil electrodes;

FIGS. 7 and 8 are, respectively, side and side section views of spaced apart windings of round and flat coil electrodes;

FIG. 9 is a diagrammatic view of a flexible coil electrode element showing two dimensions that help characterize the flexibility of the electrode element in terms of its shape.

FIG. 10 is a diagrammatic view of a flexible coil electrode element showing dimensions that help characterize the flexibility of the electrode element in terms of its ability to form tight curves of small radii.

FIG. 11 is a diagrammatic view of a flexible coil electrode element showing dimensions that help characterize the flexibility of the electrode element in terms of its ability to achieve uniform intimate contact against heart tissue.

DETAILED DESCRIPTION OF THE PREFERRED EMBODIMENTS

Figure 12:
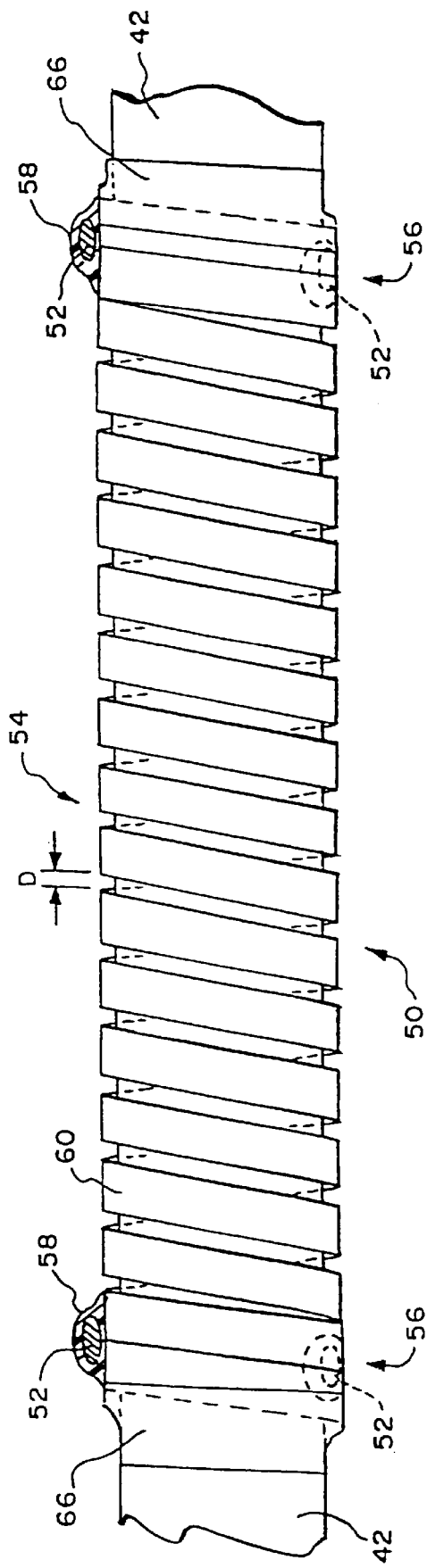
FIG. 12 is a side view of a multiple zone flexible coil electrode, which provides enhanced flexibility as well accommodates placement of temperature sensing elements.

The following is a detailed description of the best presently known modes of carrying out the invention. This description is not to be taken in a limiting sense, but is made merely for the purpose of illustrating the general principles of the invention.

This specification discloses multiple electrode structures that embody aspects of the invention. This specification also discloses tissue ablation systems and techniques using multiple temperature sensing elements that embody other aspects of the invention. The illustrated and preferred embodiments discuss these structures, systems, and techniques in the context of catheter based cardiac ablation. That is because these structures, systems, and techniques are well suited for use in the field of cardiac ablation. Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

FIGS. 1 and 2 show a flexible ablating element 10 that may be used to make lesions within the heart. The element 10 is carried at the distal end of a catheter body 12 of a probe 14. The probe 14 includes a handle 16 at the proximal end of the catheter body 12. The handle 16 and catheter body 12 carry a steering mechanism 18 for selectively bending or flexing the ablating element 10 in two opposite directions, as FIGS. 1 and 2 show.

The steering mechanism 18 can vary. In the illustrated embodiment (see FIGS. 3 and 4), the steering mechanism 18 includes a rotating cam wheel 20 with an external steering lever 22 (also see FIG. 1) carried by the handle 16. As FIG. 3 shows, the cam wheel 20 holds the proximal ends of right and left steering wires 24. The wires 24 pass through the catheter body 12 and connect to the left and right sides of a resilient bendable wire or leaf spring 26 (see FIG. 4) supported at the distal end of the catheter body 12.

Further details of this and other types of steering mechanisms for the ablating element 10 are shown in Lundquist and Thompson U.S. Pat. No. 5,254,088, which is incorporated herein by reference.

As FIG. 1 shows, forward movement of the steering lever 22 flexes or curves the ablating element 10 in one direction.

Rearward movement of the steering lever 22 flexes or curves the ablating element 10 in the opposite.

Various access techniques can be used to introduce the probe 14 into the desired region of the heart. For example, to enter the right atrium, the physician can direct the probe 14 through a conventional vascular introducer through the femoral vein. For entry into the left atrium, the physician can direct the probe 14 through a conventional vascular introducer retrograde through the aortic and mitral valves.

Alternatively, the physician can use the delivery system shown in U.S. Pat. No. 5,636,634, entitled "Systems and Methods Using Guide Sheaths for Introducing, Deploying, and Stabilizing Cardiac Mapping and Ablation Probes."

The physician can verify intimate contact between the element 10 and heart tissue using conventional pacing and sensing techniques. Once the physician establishes intimate contact with tissue in the desired heart region, the physician applies ablating energy to the element 10. The type of ablating energy delivered to the element 10 can vary. In the illustrated and preferred embodiment, the element 10 transmits electromagnetic ablating energy with a frequency below about 1.0 GHz. This type of ablating energy, which is referred to as radio frequency energy, heats tissue, mostly ohmically, without electrically stimulating it. Alternatively, the element can transmit electromagnetic ablating energy with a frequency above 1.0 GHz. This type of ablating energy, which is referred to as microwave energy, produces both ohmic and dielectric tissue heating effects.

The ablating element 10 can be conditioned to form elongated lesion patterns. These elongated lesion patterns can be continuous and extend along a straight line or along a curve. Elongated lesion patterns can be used to treat, for example, atrial fibrillation.

FIG. 2 shows one embodiment of the flexible ablating element 10. In this embodiment, a flexible body 42 carries on its exterior surface an array of spaced apart, generally flexible electrodes 44. In this embodiment, each electrode 44 comprises relatively tight spiral coils. The coil electrodes 44 can be formed by winding wire around the flexible body 42. The coil electrodes 44 can also be separately manufactured and then placed onto the flexible body 42. One manufacturing method involves machining hypotube into a series of spiral coils, thereby forming the coil electrode. Suitable machining techniques include laser cutting, chemical etching and electrical discharge machining. The coil electrodes 44 may also be manufactured by winding a wire around a mandrel and then spot welding and grinding the ends to form closed, straight ends.

The flexible body 42 is made of a polymeric, electrically nonconductive material, like polyethylene or polyurethane. It is the body 42 that carries within it the resilient bendable wire or leaf spring 26 with attached steering wires 24, as FIG. 4 shows, for flexing the body 42 and, with it, the array of electrodes 44.

The coil electrodes 44 are made of electrically conducting material. Copper alloy, platinum, or stainless steel 304, 0303, and 17-7 can be used. Drawn, filled tubing comprising a stainless steel outer tubing with a platinum or silver inner core can also be used. The electrically conducting material of the coil electrodes 44 can be coated with platinum-iridium or gold to improve its conduction properties, radiopacity and biocompatibility.

The coil electrodes 44 can be made of closely wound, generally cylindrical wire, as the coil 44(a) shown in FIGS. 5 and 6. Preferably, the coil electrodes 44 have a flat, semi-circular, or rectangular cross section, as the coil 44(b)

shown in FIGS. 5 and 6. Such a coil can be formed from flat wire or a machined hypotube. The flat cross section is preferred for several reasons.

First, with a flat cross section, the tissue contact surface area of the resulting coil electrode 44(b) can be increased in an axial direction (i.e., along the body 42) without increasing the outside diameter of the electrode 44(b). More compact and easily deployable ablating elements 10 result.

Moreover, a flat cross section permits a more efficient transmission of radio frequency ablation energy. Efficient transmission of radio frequency ablation energy by a coil electrode 44 requires keeping DC resistances between the point of electrical contact with the signal wire and any location on the coil at or below about 10 ohms. As resistances exceed about 10 ohms, the radio frequency current densities transmitted by the coil electrode 44 decrease substantially with the distance from the electrical connection. With a flat cross section, it is possible to maintain the outside and inside diameters of the wound coil electrode 44(b), and still control resistances, solely by changing the width of the windings. Furthermore, as the width of the windings increases, so can the spacing between windings, decreasing the length of the wire when wire is used to form the windings.

The overall flexibility of the element 10 is important to consistently achieve intimate contact with heart tissue along the length of the element 10 and heart tissue. Without intimate contact along the entire length of the element 10, transmission of radio frequency energy lacks uniformity, thus resulting in undesired gaps in lesion patterns. Gaps in the lesion pattern are known to be proarrhythmic and can lead to atrial flutter.

The dynamic, nonlinear nature of the endocardium complicates the matter. To consistently create intimate tissue contact, the ablation element 10 must have the capability to flexibly adapt to a wide range of contours and interior spaces within the heart.

It has been discovered that the coil electrodes 44(a) and 44(b) shown in FIGS. 5 and 6, which have windings that are very close to one another, do not always provide intimate tissue contact along the length of the element 10. Arrays of coil electrodes 44(a) and 44(b) often lack the flexibility to be easily bent into tight curves, having small curve radii. The individual coil electrodes 44(a) and 44(b) along the length of the element 10 often do not bend uniformly. Some coil electrodes 44(a) and 44(b) within the array retain straight, tangential profiles, particularly in the regions where the bend in the desired curve is most acute. Steering difficulties and gaps in lesion patterns may result.

It has been discovered that the flexibility and performance of elements 10 comprising arrays of coil electrodes 44 can be significantly enhanced by spacing the windings in a prescribed way. FIGS. 7 and 8 show a preferred embodiment of the ablating element 10 incorporating this discovery.

In this embodiment, the same flexible body 42 carries on its exterior surface an array of spaced apart lengths of helical coils forming electrodes, designated 44(c) and 44(d) in FIGS. 7 and 8. Unlike the closely spaced windings shown in FIGS. 5 and 6, in FIGS. 7 and 8, the windings in each coil electrode 44(c) and 44(d) have been spread apart by a distance D. This results from increasing the pitch of the individual wire windings forming the coil electrodes 44(c) and 44(d).

The spread-apart coil electrodes can be made of generally cylindrical wire, as the coil electrode 44(c) shown in FIGS. 7 and 8. Still, however, it is preferred that the windings in the spread-apart coil electrodes have a flat, or rectangular, cross section, as the coil electrode 44(d) shown in FIGS. 7 and 8. The same reasons set forth above for preferring a flat cross section apply.

The enhanced physical characteristics of the spread apart coil electrodes 44(c) and 44(d) in FIGS. 7 and 8, when compared to the adjacent coil electrodes 44(a) and 44(b) in FIGS. 5 and 6, can be demonstrated with respect to three physical functions. These functions differentiate flexibility among ablating elements 10 comprising arrays of spaced apart coil electrodes 44 in terms of flexed shape, degree of flexed curvature, and degree of tissue contact when flexed.

The first function ($F_S$) (see FIG. 9) relates to the shape of a flexible coil ablating element 10, when flexed. When flexed, the dimensions of the curvilinear ablating element 10 can be expressed in terms of a perpendicular distance to the first bend ($D_P$) and a maximum diameter ($D_M$). The function $F_S$ can be expressed as a ratio of these two dimensions, as follows:

$$F_S = \frac{D_P}{D_M}$$

The closer $F_S$ is to 1, the more iso-radial, or circular, the flexed structure 10 is. When $F_S \approx 1$, the flexed structure 10 becomes circular. When $F_S < 1$, the main axis of the ellipse is generally parallel to the axis of the catheter body 12, as FIG. 9 shows. When $F_S > 1$, the main axis of the ellipse is generally perpendicular to the axis of the catheter body 12.

The second function ($F_T$) (see FIG. 10) relates to the degree of curvature defined by the ablating element 10, when flexed. As FIG. 10 shows, when the element 10 is flexed, the individual coil electrode C(i) (i=1 to N, where N is the number of electrodes) will each assume its own radius of curvature ($R_{C(i)}$). $F_T$ can be expressed in terms of an average of the radii of curvature of the individual coil elements, as follows:

$$F_T = \frac{\sum_{i=1}^{i=N} R_{C(i)}}{N}$$

The magnitude of $F_T$ points to how acutely the element 10 can be flexed. As $F_T$ decreases, the smaller the overall radius of curvature for the entire flexed element 10 is, and the more the element 10 is able to be flexed into a tight curve.

The third function $F_C$ (see FIG. 11) relates to the uniformity of contact between tissue along the length of the flexed element 10. When flexed, tangents can be drawn at the edges of adjacent coil electrodes C(i) and c(i+1), designated T(i) and T(i') in FIG. 11. The tangents T(i) and T(i') intersect for each electrode C(i) to form angles $A_{T(i,i')}$. $F_C$ can be expressed as the average of the tangent angles along the length of the element, as follows:

$$F_C = \frac{\sum_{i=1}^{i=N-1} A_{T(i,i')}}{N-1}$$

Figure 14:
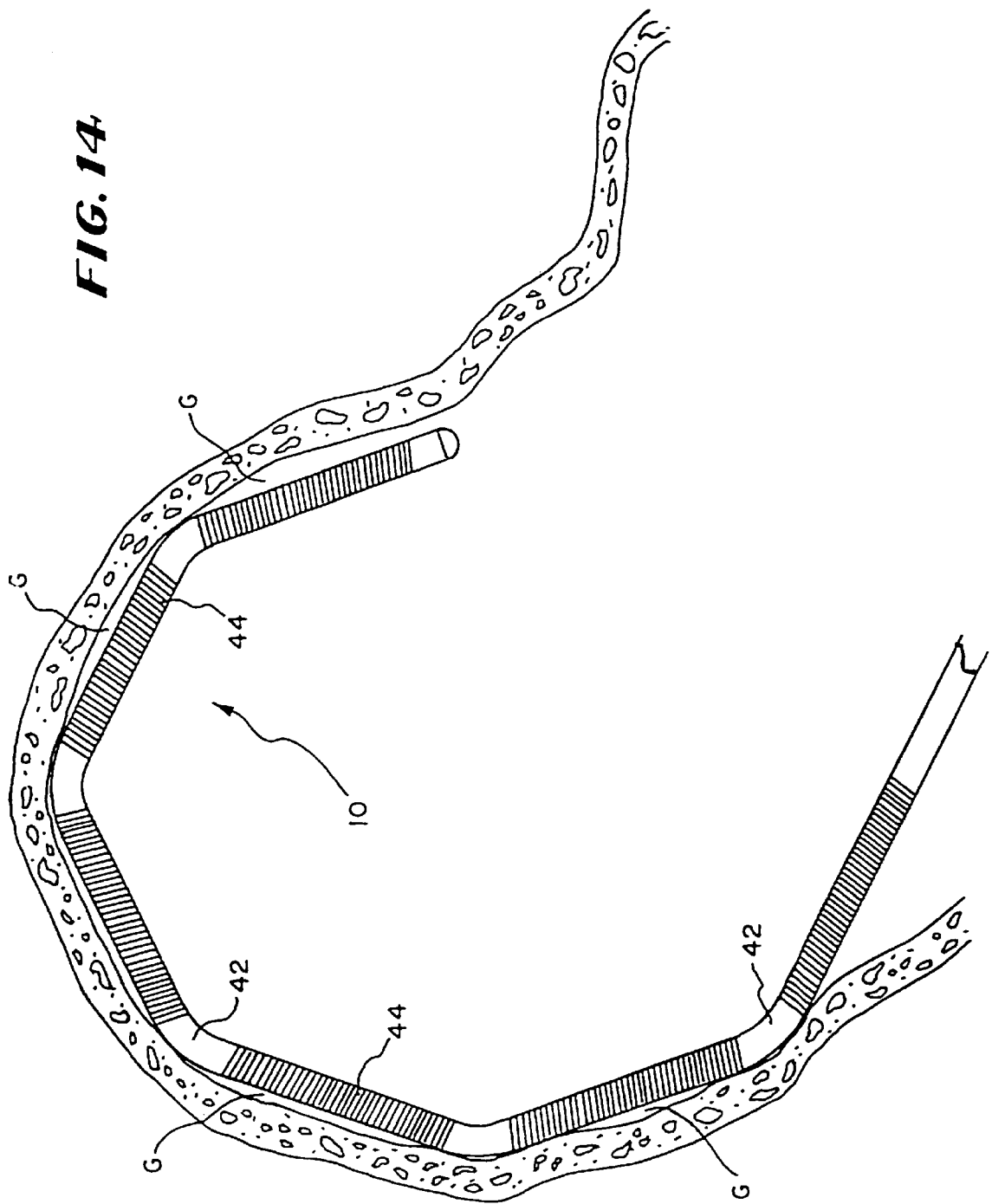
FIG. 14 is a side view of an ablation element carrying individual coil electrodes that are not sufficiently flexible to conform to the desired curve of the element, causing gaps in tissue contact.

Individual coil electrodes 44 that are not sufficiently flexible to conform to the desired curve of the element 10 will form straight sections along the length of the flexed element 10, as FIG. 14 shows. Tissue contact between successive straight sections will not be uniform. Gaps in contact (designated G in FIG. 14) can occur, creating gaps in lesions and undesired proarrhythmic effects.

Figure 15:
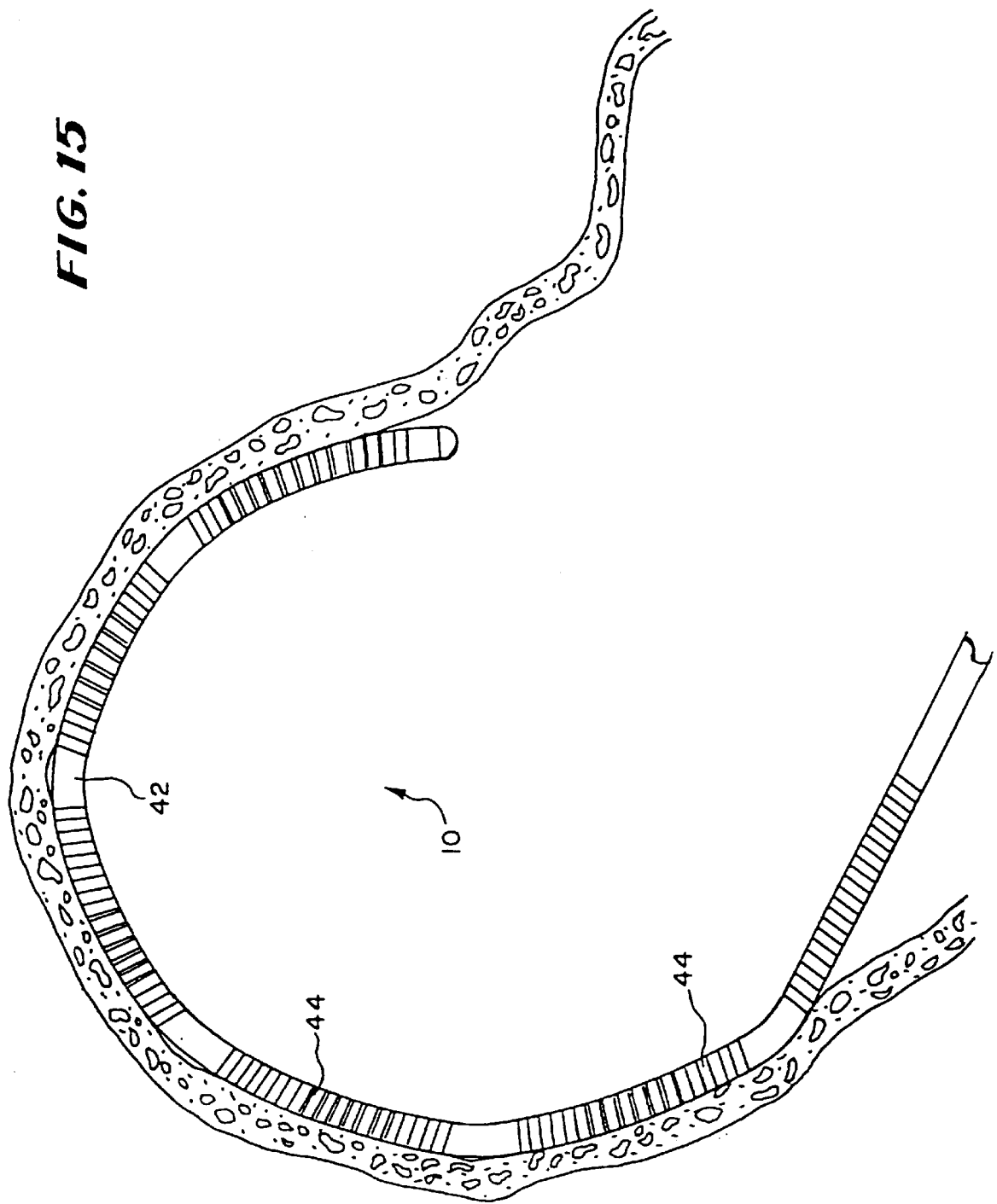
FIG. 15 is a side view of an ablation element carrying individual coil electrodes that are sufficiently flexible to conform to the desired curve of the element, creating uniform tissue contact along the length of the element.

The presence of straight sections will increase the magnitude of the tangent angles $A_{T(i, i')}$. As $F_C$ increases, the likelihood of non-uniform tissue contact along the flexed structure increases, as does the likelihood of gaps between lesions. Conversely, as $F_C$ decreases, the likelihood that the flexed element 10 will conform uniformly along its length to the curvilinear contour of tissue, without straight sections and gaps (as FIG. 15 shows), increases.

EXAMPLE

Four flexible ablation elements 10 were built for comparison, designated elements E1, E2, E3, and E4. Each ablation element E1–4 comprised six coil electrodes, each coil electrode being 12.5 mm in length. The coil electrodes were spaced apart by 2 mm. Each ablation element E1–4 used the same steering mechanism, as generally shown in FIGS. 3 and 4 and as earlier described.

The coil electrodes in ablation elements E1 and E2 used round wire having an outside diameter of 0.012 inch. In E1, the windings were adjacent, as represented by coil electrode 44(a) in FIG. 5. In E2, the windings were spaced apart, as represented by electrode 44(C) in FIG. 7. In E2, the distance D that the coil electrodes were spaced apart was ½ of the width of the wire, designated by the letter W in FIG. 7 (i.e., D=½W).

Ablation elements E3 and E4 used flat wire, 0.020 inch wide and 0.005 inch high. In E3, the windings were adjacent, as represented by electrode 44(b) in FIG. 5. In E4, the windings were spaced apart, as represented by electrode 44(d) in FIG. 7. In E4, the distance D that the coil electrodes were spaced apart was ½ of the width of the wire, also designated by the letter W in FIG. 7 (i.e., D=½W).

The physical characteristics $F_S$; $F_T$; and $F_C$ of the ablation elements E1, E2, E3, and E4 were tested. The following Tables summarize the test results:

TABLE 1

| | $F_S$ | | |
|---|---|---|---|
| | $D_P$ (inch) | $D_M$ (inch) | $F_S$ |
| E1 Round/Tight | 1.05 | 1.15 | 1.12 |
| E2 Round/Spread | 0.86 | 0.95 | 1.11 |
| E3 Flat/Tight | 0.92 | 1.11 | 1.21 |
| E4 Flat/Spread | 0.69 | 0.77 | 1.12 |

TABLE 2

| | $F_T$ |
|---|---|
| | $F_T$ |
| E1 Round/Tight | 1.23 ± 0.49 |
| E2 Round/Spread | 0.55 ± 0.24 |
| E3 Flat/Tight | 0.79 ± 0.38 |
| E4 Flat/Spread | 0.52 ± 0.26 |

TABLE 3

| | $F_C$ |
|---|---|
| | $F_C$ |
| E1 Round/Tight | 35° ± 8 |
| E2 Round/Spread | 26° ± 8 |
| E3 Flat/Tight | 31° ± 11 |
| E4 Flat/Spread | 14° ± 6 |

DC resistance (in ohms) was also measured for each ablation element, as set forth in the following Table:

TABLE 4

| | Coil Resistance |
|---|---|
| | DC Resistance (Ohms) |
| E1 Round/Tight | 3.32 ± 0.62 |
| E2 Round/Spread | 2.68 ± 0.70 |
| E3 Flat/Tight | 2.17 ± 0.16 |
| E4 Flat/Spread | 1.67 ± 0.12 |

The amount of force required to fully bend each ablation element E1; E2; E3; and E4 was measured ($F_{BEND}$) as was the force to straighten out a each bent element ($F_{UNBEND}$)' as set forth in the following table:

TABLE 5

| | Bending Forces | |
|---|---|---|
| | $F_{BEND}$ (lbf-in) | $F_{UNBEND}$ (lbf-in) |
| E1 Round/Tight | 2.90 ± 0.06 | 2.90 ± 0.10 |
| E2 Round/Spread | 2.53 ± 0.15 | 2.53 ± 0.12 |
| E3 Flat/Tight | 3.23 ± 0.06 | 3.23 ± 0.12 |
| E4 Flat/Spread | 2.87 ± 0.15 | 2.87 ± 0.12 |

The foregoing example shows:
(1) When the windings of the coil elements are brought farther apart (both round and flat wires) (Table 1), the absolute value of $F_S$ decreases, getting closer to 1.
(2) For both round and flat wires, the values of $F_T$ and $F_C$ decrease when the windings of the coil elements are spaced further apart (Tables 2 and 3).

Thus, regardless of flat or round coil configurations, spaced apart windings create an overall more flexible ablation element, which can more readily be bent into shapes having smaller radii of curvature and with greater likelihood of creating continuous zones of intimate contact with tissue, like that shown in FIG. 15. Moreover, in tightly wound coil configurations, adjacent windings can overlap during bending, which could potentially "pinch" the endocardium.

The foregoing Example also shows that the spread apart flat wire configuration (E4) achieves the lowest $F_C$ (Table 3), and thus presents the highest likelihood of a conformal curve against tissue. The force to achieve a curve using the spread flat wire configuration E4 is greater than a spread round wire (E2) (Table 5), but the curve for the spread flat wire configuration (E4) is "tighter" and thus better than for the spread round wire configuration (E2) (Table 2).

The foregoing Example demonstrates the mechanical benefits of separating the windings in the coils.

It has been determined that the benefits of greater flexibility arose when the distance D between the windings is at least ⅕ of the width W of the windings. When the windings are formed from wire, the distance D should be at least ⅕ of the width of the wire. It has been determined that spacing of less than 1/5 of the width W of the windings leads to significantly less flexibility, with greater potential for pinching tissue between the windings. The most preferred distance D is believed to be about ½ of the width W of the windings.

How far apart the windings should be spread to achieve the benefits of greater flexibility depends largely upon the desired heating effect. If additive heating effects between adjacent windings are desired to form continuous lesions between the windings, the upper spacing limit becomes the distance at which the desired additive heating effect is observed to diminish. The diminishing of the additive heating effect can be determined empirically or mathematically under the desired operating conditions and geometries.

When the spacing between the electrodes is equal to or less than about 3 times the smaller of the diameters of the electrodes, the simultaneous emission of energy by the electrodes creates an elongated continuous lesion pattern in the contacted tissue area due to the additive effects. Similar effects are obtained when the spacing between the electrodes is equal to or less than about 2 times the longest of the lengths of the electrodes.

To consistently form long, thin, continuous curvilinear lesion patterns, additional spatial relationships among the electrodes must be observed. When the length of each electrode is equal to or less than about 5 times the diameter of the respective electrode, the curvilinear path that the probe takes should create a distance across the contacted tissue area that is greater than about 8 times the smaller of the diameters of the electrodes. The simultaneous application of energy will form a continuous elongate lesion pattern that follows the curved periphery contacted by the probe, but does not span across the contacted tissue area. The same effect will be obtained when the length of each electrode is greater than about 5 times the diameter of the respective electrode, and the curvilinear path that support element takes should create a radius of curvature that is greater than about 4 times the smallest the electrode diameters. Of course, the spacing between the electrodes must be such that additive heating effects are created.

Taking the above considerations into account, it has been found that adjacent electrode segments having lengths of less than about 2 mm do not consistently form the desired continuous lesions. Flexible electrode elements can range from 2 mm to 50 mm in length and are preferably 12.5 mm in length with 2 to 3 mm spacing. The diameter of the electrodes and underlying flexible body can vary from about 4 french to about 10 french in catheter-type probes.

Various ways to control the characteristics of lesions formed by the ablating elements 10 are disclosed in detail in U.S. application Ser. No. 08/287,192, filed Aug. 8, 1994, entitled "Systems and Methods for Forming Elongated Lesion Patterns in Body Tissue Using Straight or Curvilinear Electrode Elements" (now abandoned) and in U.S. application Ser. No. 08/439,824, filed May 12, 1995, entitled "Systems and Methods for Controlling Tissue Ablation Using Multiple Temperature Sensing Elements" (now abandoned), both of which are incorporated herein by reference.

Above-identified U.S. application Ser. No. 08/439,824 shows the use of temperature sensing elements to measure temperatures along the length of the ablation element 10. As disclosed in this prior application, the positioning of the temperature sensing elements on the electrode elements 10 is important for achieving reliable temperature sensing, particularly when the length of an individual coil on the element 10 exceeds about 10 mm, as contemplated in the preferred embodiment of this application.

FIG. 12 shows a preferred embodiment of a coil electrode 50 designed for enhanced flexibility as well as to accommodate optimal placement of temperature sensing elements 52. As FIG. 12 shows, the coil electrode 50 comprises two zones 54 and 56.

The first zone 54 represents the majority of the electrode 50, occupying its entire mid portion. The first zone 54 comprises spaced apart windings to provide enhanced flexibility, as already described.

The second zone 56 occupies each edge of the coil electrode 50. The second zone 56 comprises a region where the windings are closely adjacent to each other. The closeness of the windings provides a support structure for the temperature sensing element 52.

As FIG. 12 shows, the temperature sensing elements 52 are threaded up through the windings in each second zone 56 to lay upon its exterior surface. In the illustrated embodiment, the sensing elements 52 comprise thermocouples, and each is encapsulated in an epoxy or PTFE coating 58. However, thermistors can be used.

Preferably, as shown in phantom lines in FIG. 12, the temperature sensing elements 52 can be secured to the inside surface of each second zone 56. Still alternatively, the sensing elements 52 can be sandwiched between the inside surface of the second zones 56 and the underlying flexible body 42.

The two zone structure of the coil electrode 50 shown in FIG. 12 allows placement of temperature sensing elements 52 at the side edges 60 of the electrode 50. These edges 60 are where the electrode 50 abuts the underlying, non-electrically conductive support body 42. RF current densities are high at these edges 60, because the edges 60 are regions where electrical conductivity is discontinuous. The resulting rise in current density at the electrode edges 60 generates localized regions of increased power density and, therefore, regions where higher temperatures exist. Given the elongated size of the electrode 50, temperature sensing elements 52 should preferably be located in these edge regions where high localized temperatures are to be expected. The closely spaced windings at the second region 56 accommodate such placement, without detracting from the overall flexibility that the first region 54 provides.

In a preferred embodiment (as FIG. 12 shows), a thin strip 66 of electrically insulating material (for example, an electrically nonconducting adhesive) is applied about the body 42 immediately next to the second regions 56. It has been observed that the presence of this electrically nonconducting strip 56 helps to minimize the presence of edge effect currents, which tend to be more pronounced in coil electrodes than other electrode structures.

Figure 13:
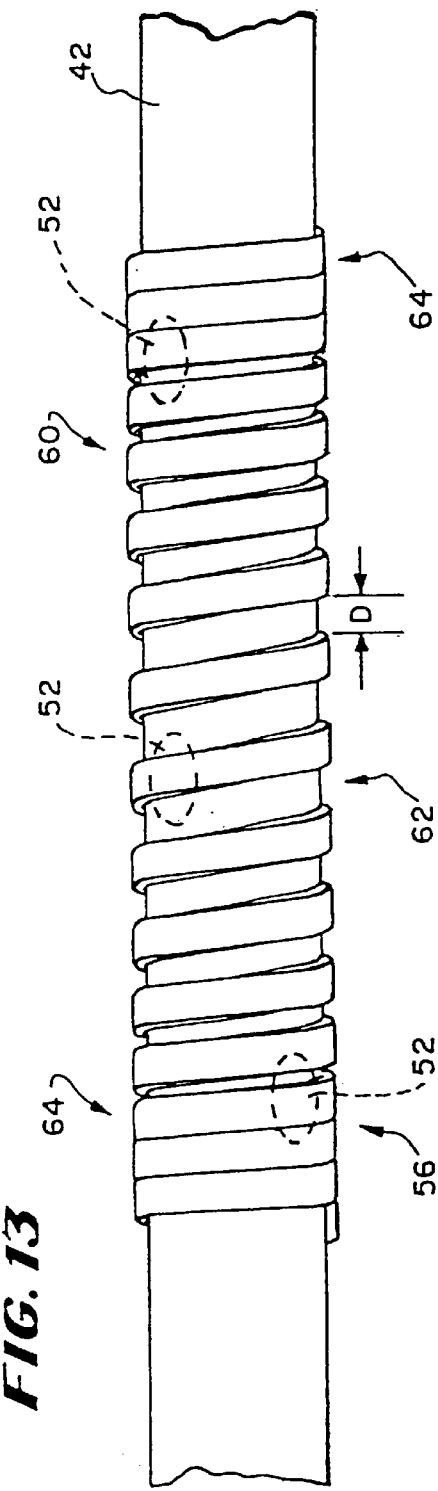
FIG. 13 is a side view of an alternative embodiment of a multiple zone flexible coil electrode.

FIG. 13 shows an alternative embodiment of a coil electrode 60 designed for enhanced flexibility as well as to accommodate optimal placement of temperature sensing elements 52. FIG. 13 is similar to FIG. 12, in that the coil electrode 60 comprises at least two zones 62 and 64 of different spacing D between coil windings. In FIG. 12, the spacing D in the interior zone 54 is generally uniform, maintaining a distance at least 1/5 of the width of the wire. In FIG. 13, the spacing D in the interior zone 62 is at least 1/5 of the width of the wire, but the actual distance D varies along the interior zone 62. As FIG. 13 shows, the spacing D in the interior zone 62 decreases progressively from the mid point of the coil 60 toward the edge zones 64, where the windings are closely spaced (i.e., less than 1/5 of the width of the windings) to support temperature sensing elements 52.

Alternatively, the spacing D can vary along the interior zone 62 in a random fashion, while still observing the minimum spacing of ⅕ of the width of the windings. Practically speaking, it is to be expected that the spacing D will not be perfectly uniform or perfectly progressive, but will vary along the interior zone 62, because of normal tolerance deviations in the manufacturing process.

As FIG. 13 also shows, the interior zone 62 (or, in FIG. 12, zone 54) could also carry a temperature sensing element 52. The use of a third, more centrally located temperature sensing element 52 is preferred when temperature prediction algorithms are used, as disclosed in U.S. application Ser. No. 08/439,824, as previously identified.

Figure 16:
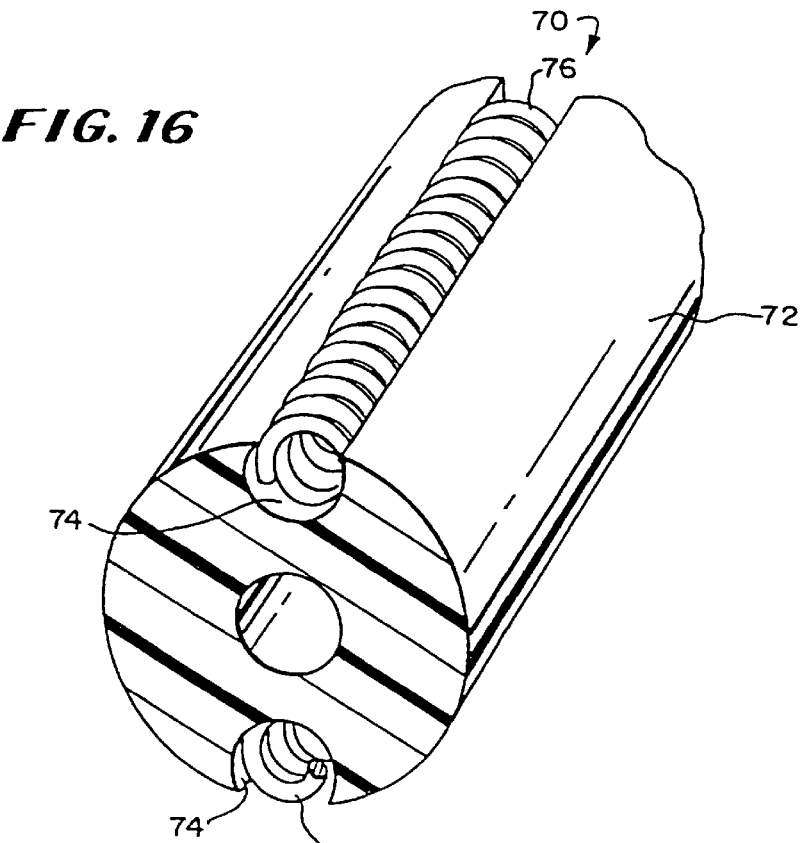
FIG. 16 is a perspective section view of an alternative embodiment of a flexible ablation element carrying spaced apart coil electrodes in sidelong channels.
Figure 17:
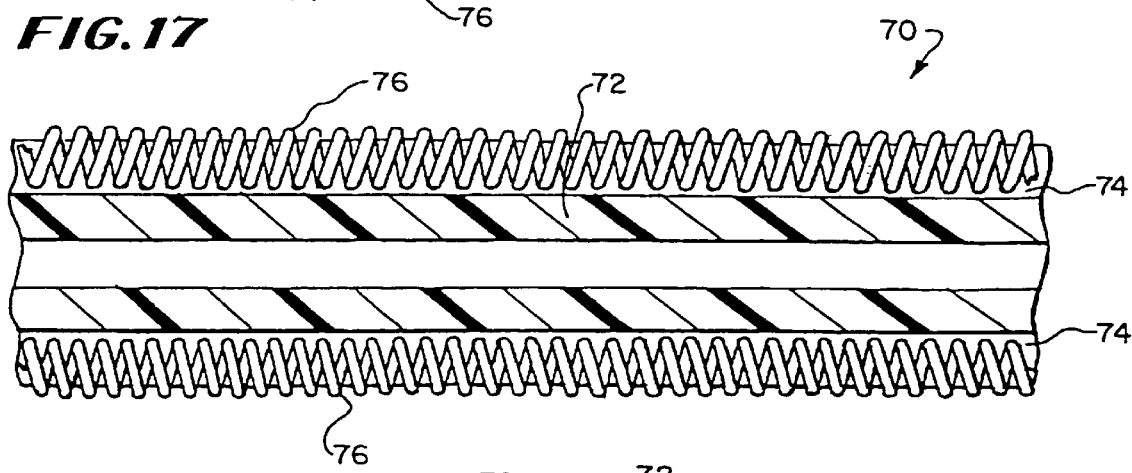
FIG. 17 is a side section view of the ablation element shown in FIG. 16, the ablation element being shown in an unflexed condition.
Figure 18:
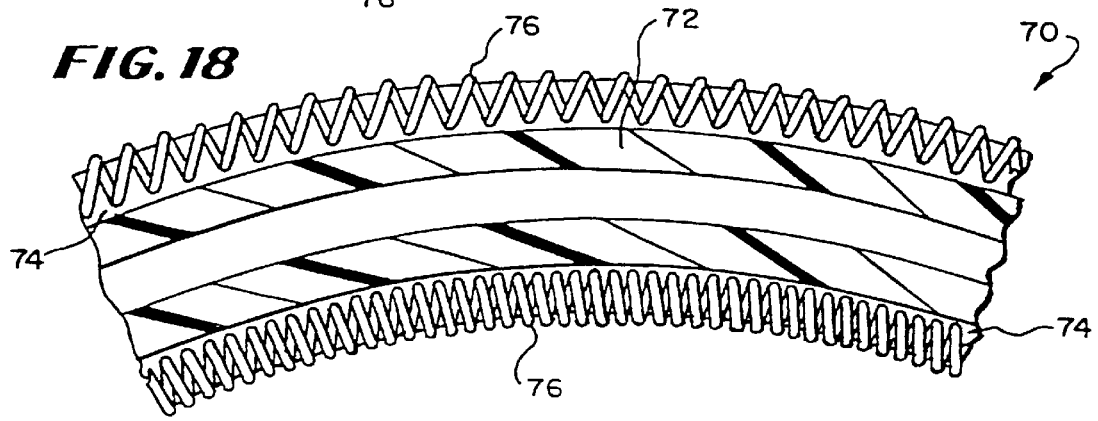
FIG. 18 is a side section view of the ablation element shown in FIG. 16, the ablation element being shown in a flexed condition.

FIGS. 16 to 18 show an alternative embodiment of a spaced-apart coil electrode 70 that achieves the benefits of the invention. In this embodiment, a flexible catheter body 72 includes an opposed pair of side channels 74 along its length. Each side channel 72 carries a spiral wound wire coil 76. The windings of the coil are spaced apart, in accordance with the invention, by at least ⅕ of the width of the windings.

The catheter body 72 carries within a resilient bendable wire or leaf spring with attached steering wire, as shown in FIG. 4 (but which is not shown in FIGS. 16 to 18). As described in preceding embodiments (and as FIG. 18 shows), pulling on the steering wires flexes the body 72 in opposite directions along the axes of the channels 72, thereby also bending the wound coils 76. The spaced apart nature of the coils 76 provides enhanced flexibility, in the manner already described.

Regarding the several embodiments of the invention already discussed, it should be noted that, in addition to the mechanical advantage of enhanced flexibility, there are also considerable electrical advantages that attend the use of a coil electrode with spaced apart windings. A coil electrode with windings spaced apart in accordance with the invention provides a more uniform thermal profile in tissue heated by coil. This is because the current flow through the spaced apart windings is more uniform than it otherwise would be. The result is less temperature differentials along the length of the coil and the elimination of "hot spots."

The provision of spaced apart windings in a coil implemented in accordance with the invention also makes possible the reduction of edge current effects. By coupling the energy signal wire 78 (see FIG. 8) to the mid portion of a spaced apart coil 44(d), higher resistance between the coil mid portion and the edge of the coil can be achieved. This, in turn, decreases current density at the edge, thereby decreasing edge current effects. Without a spaced apart coil, one would have to turn to other techniques to reduce edge current effects, such as changing the length of the coil, thinning the cross sectional area of the coil, or changing the material of the coil.

The invention therefore makes possible the attainment of both mechanical and electrical advantages beneficial to tissue ablation.

Although the present invention has been described in terms of the preferred embodiment above, numerous modifications and/or additions to the above-described preferred embodiments would be readily apparent to one skilled in the art. It is intended that the scope of the present invention extends to all such modifications and/or additions.

We claim:

1. A device for ablating body tissue, comprising:
    a support body,
    an electrode carried by the support body including a plurality of adjacent windings and having at least one edge portion adjoining the support body and an other portion spaced away from the at least one edge portion, the adjacent windings being spaced closer together near the at least one edge portion than along the other portion of the electrode, and
    a connection coupling the electrode to a source of ablation energy.

2. A device according to claim 1, wherein the electrode has a rectilinear cross section.

3. A device according to claim 1, wherein the electrode has a circular cross section.

4. A device according to claim 1, wherein spacing between the adjacent windings in the other portion of the electrode varies.

5. A device according to claim 1, wherein spacing between the adjacent windings in the other portion of the electrode is generally uniform.

6. A device according to claim 1, further comprising:
    at least one temperature sensing element on the electrode.

7. A device according to claim 1, further comprising:
    a temperature sensing element near the at least one edge portion of the electrode.

8. A device according to claim 1, wherein the windings have a width and the adjacent windings are spaced apart by at least ⅕ of the width except near the at least one edge portion, where the adjacent windings are spaced closer than ⅕ of the width.

9. A device according to claim 1, wherein the windings have a width and the adjacent windings are spaced apart by about ½ of the width except near the at least one edge portion, where the adjacent windings are spaced closer than ⅕ of the width.

10. A device according to claim 1, wherein the connection couples the electrode to a source of radio frequency ablation energy.

11. A device according to claim 1, wherein the support body has an axis and is flexible, the device further comprising:
    an element for flexing the support body relative to the axis and, with it, the electrode.

12. A device for ablating body tissue, comprising:
    a flexible support body having an axis,
    an electrode carried by the support body including a plurality of adjacent windings having at least one edge portion adjoining the support body, the windings having a width, the adjacent windings being spaced apart by a distance at least ⅕ of the width except near the at least one edge portion, where the adjacent windings are spaced closer than ⅕ of the width,
    an element for flexing the support body relative to the axis and, with it, the electrode, and
    a connection coupling the electrode to a source of ablation energy.

13. A device according to claim 12, wherein the electrode comprises wire wound about the flexible support body.

14. A device according to claim 12, wherein the electrode has a rectilinear cross section.

15. A device according to claim 12, wherein the electrode has a circular cross section.

16. A device according to claim 12, wherein the connection couples the electrode to a source of radio frequency ablation energy.

17. A device according to claim 12, further comprising:
    at least one temperature sensing element on the electrode.

18. A device for ablating body tissue, comprising:
    a flexible support body having an axis, at least two mutually spaced apart electrodes carried by the support body, each electrode including a plurality of adjacent windings and having opposite edges adjoining the support body, the adjacent windings of each electrode being spaced farther apart away from the opposite edges than at the opposite edges, an element for flexing the support body relative to the axis and, with it, the electrodes, and a connection coupling the electrodes to a source of ablation energy.

19. A device according to claim 18, wherein the windings have a width and the adjacent windings of each electrode are spaced apart by at least ⅕ of the width except near the opposite edges, where the adjacent windings are spaced closer than ⅕ of the width.

20. A device according to claim 18, wherein the windings have a width and the adjacent windings of each electrode are spaced apart by about ½ of the width except near the opposite edges, where the adjacent windings are spaced closer than ⅕ of the width.

21. A device according to claim 18, wherein spacing varies between the adjacent windings away from the opposite edges.

22. A device according to claim 18, wherein spacing is generally uniform between the adjacent windings away from the opposite edges.

23. A device according to claim 18, wherein the windings have a rectilinear cross section.

24. A device according to claim 18, wherein the windings have a circular cross section.

25. A device according to claim 18, wherein the connection couples the electrodes to a source of radio frequency ablation energy.

26. A device according to claim 18, further comprising:
at least one temperature sensing element near at least one of the opposite edges of at least one of the electrodes.

27. A device for ablating body tissue comprising
a flexible support body having an axis,
at least two mutually spaced apart electrodes carried by the support body, each electrode including a plurality of adjacent windings and having opposite edges adjoining the support body, the windings of each electrode being spaced farther apart away from the opposite edges that at the opposite edges,
an element for flexing the support body relative to the axis and, with it, the electrodes,
a connection coupling the electrodes to a source of ablation energy, and
at least one temperature sensing element on each electrode near at least one of the opposite edges of each electrode.

28. A device according to claim 27, wherein there is at least one temperature sensing element on each electrode near both opposite edges of each electrode.

29. A device according to claim 28, further comprising:
a temperature sensing element on each electrode between the opposite edges of each electrode.

30. A device according to claim 27, wherein the windings have a width and the adjacent windings of each electrode are spaced apart by at least ⅕ of the width except near the opposite edges of each electrode, where the adjacent windings are spaced closer than ⅕ of the width.

31. A device according to claim 27, wherein spacing varies between the adjacent windings away from the opposite edges of each electrode.

32. A device according to claim 27, wherein spacing is generally uniform between the adjacent windings away from the opposite edges of each electrode.

33. A device according to claim 27, wherein the windings have a rectilinear cross section.

34. A device according to claim 27, wherein the windings have a circular cross section.

35. A device according to claim 27, wherein the connection couples the electrodes to a source of radio frequency ablation energy.

36. A device for ablating body tissue, comprising:
a flexible support body having an axis,
an electrode carried by the support body including a plurality of adjacent windings, the windings having a width and adjacent windings being spaced apart by a distance at least ⅕ of the width, the electrode having opposite edges adjoining the flexible support body and a mid region extending without interruption between the opposite edges, and
a signal wire coupled to the mid region of the electrode to couple the electrode to a source of ablation energy.

37. A device according to claim 36, further comprising:
an electrically non conducting material applied to the opposite edges and the flexible support body adjoining the opposite edges.

38. A method of ablating body tissue, comprising the steps of:
deploying in the body an electrode including a plurality of adjacent windings carried by a flexible support having an axis, the windings having a width and at least one edge portion adjoining the flexible support, the adjacent windings being spaced apart by a distance at least ⅕ of the width except near the at least one edge portion, where the adjacent windings are spaced closer than ⅕ of the width,
flexing the support relative to the axis and, with it, the electrode,
coupling the electrode to a source of ablation energy, and
transmitting the ablation energy to form a lesion pattern that follows the flexed electrode.

39. A method according to claim 38, wherein the coupling step includes coupling the electrode to a source of radio frequency ablation energy.

40. A method according to claim 38, further comprising the step of:
sensing temperature using a sensor carried on the flexible support.

41. A method of ablating body tissue, comprising the steps of:
deploying in the body at least two mutually spaced apart electrodes carried by a flexible support, each electrode including a plurality of adjacent windings and having opposite edges adjoining the support, the support having an axis, the windings of each electrode being spaced farther apart away from the opposite edges that at the opposite edges,
flexing the support relative to the axis and, with it, the electrodes, and
coupling the electrodes to a source of ablation energy.

42. A method according to claim 41, wherein the coupling step includes coupling the electrodes to a source of radio frequency ablation energy.

43. A method according to claim 41, further comprising:
the step of sensing temperature using a sensor carried on the flexible support.

44. A device for ablating body tissue, comprising:
a flexible support body having an axis, a circumference and an exterior and a longitudinally extending channel on the exterior of the support body extending around less than the entire circumference, an electrode carried within the channel including a plurality of adjacent windings and having at least one edge portion adjoining the support body, the windings having a width and adjacent windings being spaced apart by a distance at least ⅕ of the width, an element for flexing the support body relative to the axis and, with it, the electrode, and a connection coupling the electrode to a source of ablation energy.

45. A device according to claim 44, wherein the windings have a rectilinear cross section.

46. A device according to claim 44, wherein the windings have a circular cross section.

47. A device for ablating body tissue, comprising:

a flexible support body having an axis, at least two mutually spaced apart electrodes carried by the support body, each electrode including a plurality of adjacent windings and having opposite end edges adjoining the support body, an element for flexing the support body relative to the axis and, with it, the electrodes, a connection coupling the electrodes to a source of ablation energy, and at least one temperature sensing element substantially abutting and in thermal contact with at least one of the opposite end edges of each electrode.

48. A device according to claim 47, further comprising:

a temperature sensing element on each electrode between the opposite edges of each electrode.

49. A device according to claim 47, wherein the electrode has a rectilinear cross section.

50. A device according to claim 47, wherein the electrode has a circular cross section.

51. A device according to claim 47, wherein the connection couples the electrode to a source of radio frequency ablation energy.

52. A method of ablating body tissue, comprising the steps of:

deploying in the body an electrode carried by a flexible support including a plurality of adjacent windings and having at least one edge portion adjoining the support body and an other portion spaced away from the at least one edge portion, the adjacent windings being spaced closer together near the at least one edge than along the other portion of the electrode, flexing the support relative to the axis and, with it, the electrode, coupling the electrode to a source of ablation energy, transmitting the ablation energy from the electrode to form a lesion pattern that follows the flexed electrode.

53. A method according to claim 52, wherein the coupling step includes coupling the electrode to a source of radio frequency ablation energy.

54. A method according to claim 52, further comprising the step of:

sensing temperature using a sensor carried on the flexible support.

* * * * *

UNITED STATES PATENT AND TRADEMARK OFFICE
CERTIFICATE OF CORRECTION

PATENT NO. : 6,030,382
DATED : February 29, 2000
INVENTOR(S) : Sidney D. Fleischman, et al.

It is certified that error appears in the above-identified patent and that said Letters Patent is hereby corrected as shown below:

On the title page, item 54 and in column 1, line 1, (Title), replace "ABLATIN" with --ABLATION--.

Signed and Sealed this

Sixth Day of February, 2001

Attest:

Q. TODD DICKINSON

*Attesting Officer*  *Director of Patents and Trademarks*